(12) United States Patent
Raphael et al.

(10) Patent No.: US 7,993,409 B2
(45) Date of Patent: Aug. 9, 2011

(54) LIP IMPLANT AND METHOD FOR INSERTION

(75) Inventors: Peter Raphael, Plano, TX (US); Scott Harris, Dallas, TX (US)

(73) Assignee: Surgisil, L.L.P., Plano, TX (US)

( * ) Notice: Subject to any disclaimer, the term of this patent is extended or adjusted under 35 U.S.C. 154(b) by 500 days.

(21) Appl. No.: 11/929,267

(22) Filed: Oct. 30, 2007

(65) Prior Publication Data
US 2008/0058928 A1 Mar. 6, 2008

Related U.S. Application Data

(63) Continuation of application No. 10/792,984, filed on Mar. 4, 2004, now Pat. No. 7,344,566, which is a continuation-in-part of application No. 10/384,229, filed on Mar. 7, 2003, now Pat. No. 7,008,455.

(51) Int. Cl.
*A61F 2/04* (2006.01)
(52) U.S. Cl. .................................................. 623/23.64
(58) Field of Classification Search ............... 623/11.11, 623/15.11, 23.64, 23.72
See application file for complete search history.

(56) References Cited

U.S. PATENT DOCUMENTS

| | | | |
|---|---|---|---|
| 4,157,085 A | 6/1979 | Austad | |
| 4,481,001 A | 11/1984 | Graham et al. | |
| 5,030,232 A | 7/1991 | Pham | |
| 5,195,951 A | 3/1993 | Giampapa | |
| 5,258,028 A | 11/1993 | Ersek et al. | |
| 5,413,600 A | 5/1995 | Mittelman | |
| 5,496,371 A | 3/1996 | Eppley et al. | |
| 5,571,182 A | 11/1996 | Ersek et al. | |
| 5,578,050 A | 11/1996 | Webb | |
| 5,607,477 A | 3/1997 | Schindler et al. | |
| 5,782,913 A | 7/1998 | Schindler et al. | |
| 5,941,909 A | 8/1999 | Purkait | |
| 5,941,910 A | 8/1999 | Schindler et al. | |
| 6,083,262 A | 7/2000 | Caravel | |
| 6,083,912 A | 7/2000 | Khouri | |
| 6,129,761 A | 10/2000 | Hubbell | |
| 6,277,150 B1 | 8/2001 | Crawley et al. | |
| 7,008,455 B2 | 3/2006 | Raphael et al. | |
| 7,329,286 B2 | 2/2008 | Raphael et al. | |
| 7,344,566 B2 | 3/2008 | Raphael et al. | |
| 2002/0019670 A1 | 2/2002 | Crawley et al. | |
| 2004/0073318 A1 | 4/2004 | Reinmuller | |

FOREIGN PATENT DOCUMENTS

| | | |
|---|---|---|
| DE | 4414103 A1 | 10/1995 |
| WO | WO 95/34256 | 12/1995 |
| WO | WO 99/51164 | 10/1999 |
| WO | WO 00/33771 | 6/2000 |
| WO | WO 2004/080337 A2 | 9/2004 |

OTHER PUBLICATIONS

European Patent Office, Supplementary European Search Report, issued in Application No. EP04717985, dated Nov. 12, 2008.

(Continued)

*Primary Examiner* — William H. Matthews
(74) *Attorney, Agent, or Firm* — Haynes and Boone, LLP

(57) ABSTRACT

A lip implant having first and second regions is described. The lip implant includes a first region formed of a liquid, solid, or a gas and a second region formed of a solid material. Also described is a lip implant having an elongated cross-section. A method for insertion of the implant is also described along with the instrumentation facilitating its insertion.

10 Claims, 2 Drawing Sheets

OTHER PUBLICATIONS

Examination Report dated Aug. 11, 2008, by IP Australia, regarding Australian Patent Application No. 2004220602.
Examination Report dated Jun. 2, 2009, by IP Australia, regarding Australian Patent Application No. 2004220602.
Correspondence from foreign counsel dated Dec. 19, 2008, regarding Office Action issued in connection with Mexican Patent Application No. PA/a/2005/009527.
Correspondence from foreign counsel dated Aug. 18, 2009, regarding Office Action issued in connection with Mexican Patent Application No. PA/a/2005/009527.
Correspondence from foreign counsel dated Aug. 18, 2009, regarding Office Action issued in connection with Mexican Patent Application No. PA/a/2005/003784.
Examination Report dated Nov. 10, 2009, by the European Patent Application, regarding European Patent Application No. 04717985.8.
International Searching Authority "International Search Report," Sep. 27, 2004, 6 pgs., International Serial No. PCT/US2004/006722.
International Searching Authority "Written Opinion," Sep. 27, 2004, 5 pgs; International Serial No. PCT/US2004/006722.
International Preliminary Examining Authority, "International Preliminary Report on Patentability," Aug. 1, 2005, 6 pgs., International Serial No. PCT/US2004/006722.
William H. Matthews "Office Action," Jul. 13, 2004, 6 pgs., U.S. Appl. No. 10/384,229, U.S. Patent and Trademark Office.
William H. Matthews, "Office Action," Oct. 20, 2004, 7 pgs., U.S. Appl. No. 10/384,229, U.S. Patent and Trademark Office.
William H. Matthews, "Office Action," Apr. 28, 2005, 7 pgs., U.S. Appl. No. 10/384,229, U.S. Patent and Trademark Office.
William H. Matthews, "Notice of Allowability," Aug. 4, 2005, 1 pg., U.S. Appl. No. 10/384,229, U.S. Patent and Trademark Office.
William H. Matthews, "Notice of Allowance," Aug. 4, 2005, 3 pgs., U.S. Appl. No. 10/384,229, U.S. Patent and Trademark Office.
William H. Matthews, "Supplemental Notice of Allowability," Aug. 8, 2005, 3 pgs., U.S. Appl. No. 10/384,229, U.S. Patent and Trademark Office.
William H. Matthews, "Office Action," Feb. 1, 2007, 6 pgs., U.S. Appl. No. 10/792,984, U.S. Patent and Trademark Office.
William H. Matthews, "Office Action," May 3, 2007, 6 pgs , U.S. Appl. No. 10/792,984, U.S. Patent and Trademark Office.
William H. Matthews, "Interview Summary," Jun. 5, 2007, 4 pgs., U.S. Appl. No. 10/792,984, U.S. Patent and Trademark Office.
William H. Matthews, "Notice of Allowability," Nov. 28, 2007, 3 pgs., U.S. Appl. No. 10/792,984, U.S. Patent and Trademark Office.
William H. Matthews, "Notice of Allowance," Nov. 28, 2007, 3 pgs., U.S. Appl. No. 10/792,984, U.S. Patent and Trademark Office.
William H. Matthews, "Office Action," Feb. 1, 2007, 5 pgs., U.S. Appl. No. 11/234,358, U.S. Patent and Trademark Office.
William H. Matthews, "Office Action," Jun. 5, 2007, 8 pgs, U.S. Appl. No. 11/234,358, U.S. Patent and Trademark Office.
William H. Matthews, "Interview Summary," Aug. 31, 2007, 3 pgs., U.S. Appl. No. 11/234,358, U.S. Patent and Trademark Office.
William H. Matthews, "Notice of Allowability," Oct. 25, 2007, 4 pgs., U.S. Appl. No. 10/234,358, U.S. Patent and Trademark Office.
William H. Matthews, "Notice of Allowance," Oct. 25, 2007, 3 pgs., U.S. Appl. No. 10/234,358, U.S. Patent and Trademark Office.
Edward O. Terino, M.D. and Robert S. Flowers, M.D., *The Art of Alloplastic Facial Contouring*; 2000, 4 pgs.; Mosby, St. Louis, MO.
A. Oxfort-Thumser, Office Communication under Rule 71(3) in European Patent Application No. EP 04717985.8; Aug. 9, 2010, 17pgs., European Patent Office, Munich, Germany.

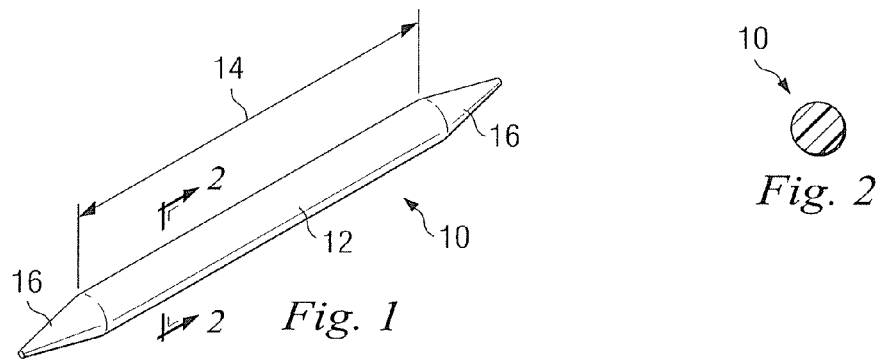
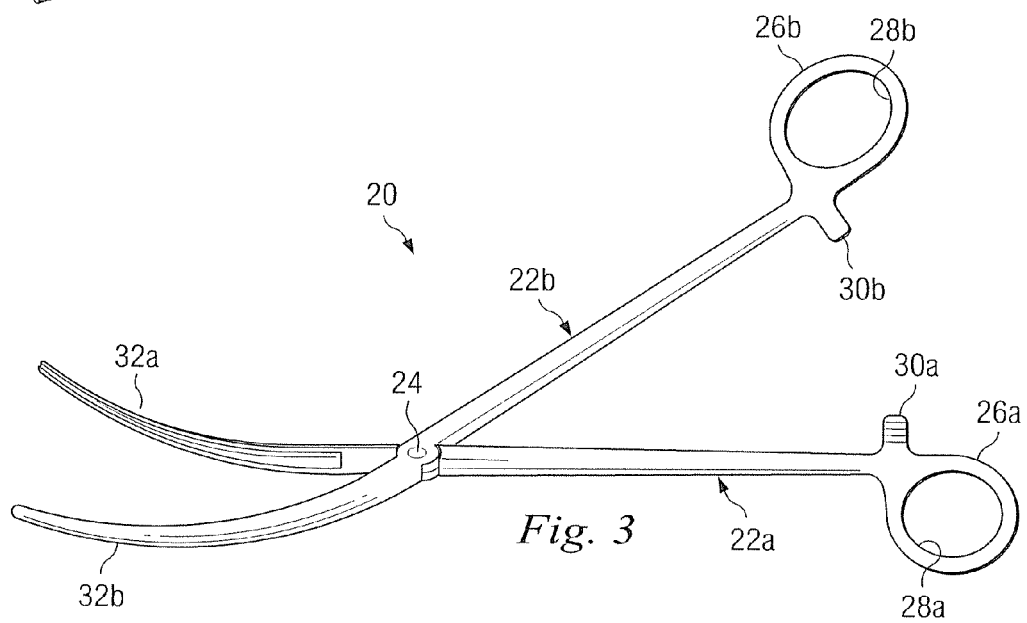
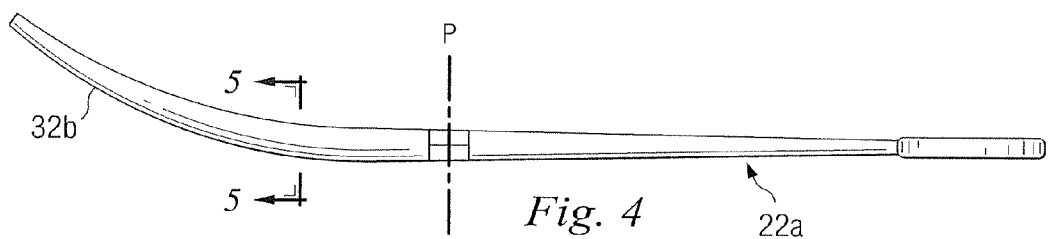
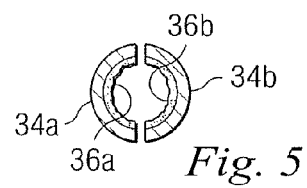

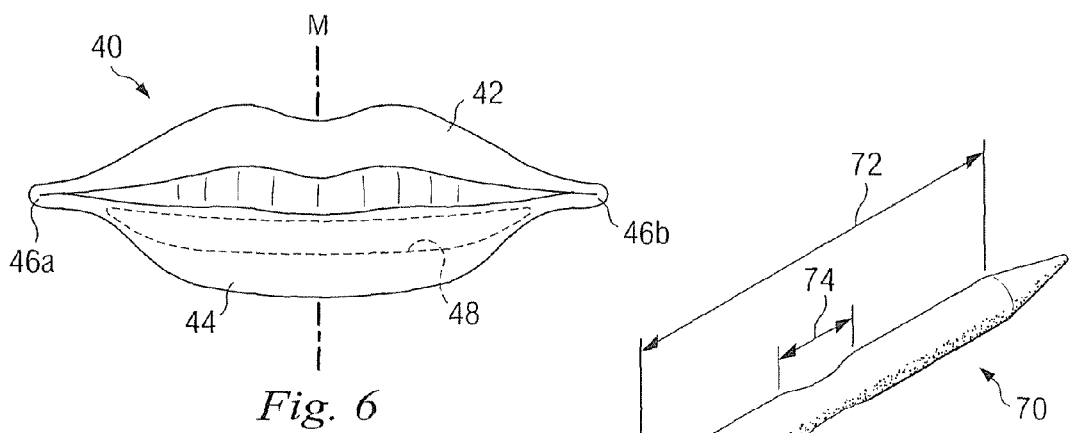
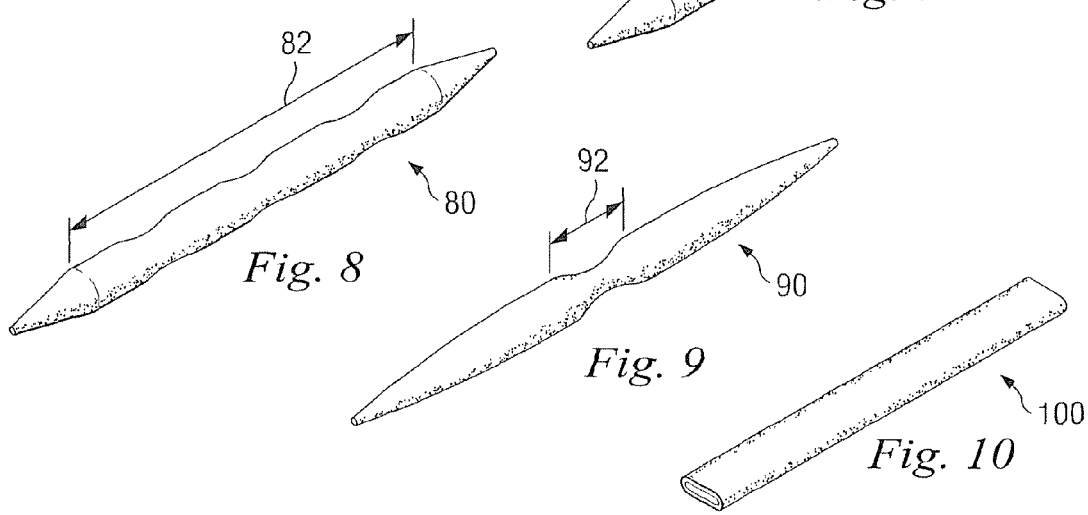
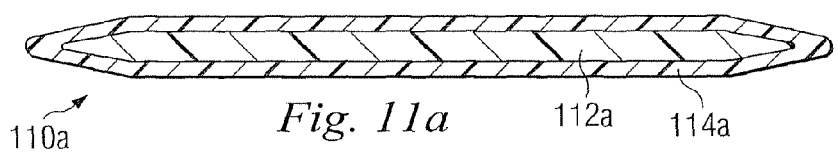
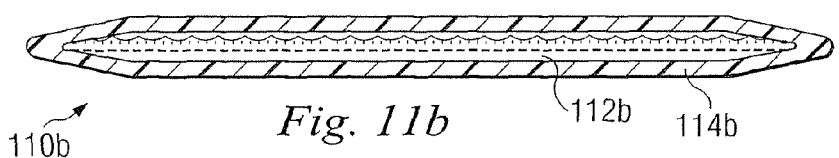
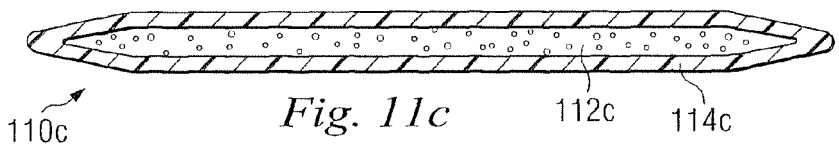

LIP IMPLANT AND METHOD FOR INSERTION

CROSS-REFERENCE TO RELATED APPLICATIONS

This application is a continuation of application Ser. No. 10/792,984, filed on Mar. 4, 2004, which issued as U.S. Pat. No. 7,344,566 on Mar. 18, 2008, and which is a continuation-in-part of application Ser. No. 10/384,229, filed on Mar. 7, 2003, which issued as U.S. Pat. No. 7,008,455 on Mar. 7, 2006.

BACKGROUND

The present disclosure relates generally to a lip implant, and more particularly to a lip implant, which may be used for lip augmentation or enhancement.

Within the field of Plastic Surgery, soft tissue augmentation has long been in popular demand by people wishing to enhance their physical appearance. More recently, lip augmentation, i.e. increasing the fullness of the lips, has become a viable entity.

Currently, there are a variety of materials and methods used for lip augmentation. Some of the current techniques provide for temporary lip augmentation via injection of various materials into the lip such as fat, collagen, hyaluronic acid, and particulated dermis or fascia. One of the disadvantages of such temporary techniques is the need for the patient to periodically undergo additional procedures to maintain the lip fullness.

Other techniques, such as liquid silicone injections, provide a more permanent lip augmentation. However, liquid silicone injections may be complicated by skin ulceration, long-term nodularity and granuloma formation, and chronic cellulitis. Furthermore, it is inherently difficult to remove liquid silicone from the lips should a problem arise or should the patient desire removal. That is, reversibility is difficult or impossible.

Another permanent lip augmentation technique is the implantation of expanded polytetraflouroethylene (PTFE) such as Gore-Tex® strips or tubular forms of PTFE such as Softform® and Ultrasoft™. Expanded PTFE utilizes the concept of tissue ingrowth into the porous wall of the implant. While beneficial in some areas of the body, implantation of such material into the lips can be complicated by tissue adherence to the implant. Tissue ingrowth may result in restriction of lip excursion and result in an abnormal appearance during facial expression. Furthermore, fluid may accumulate inside the tubular forms of PTFE, thereby resulting in an unacceptable incidence of postoperative surgical infection and subsequent loss of implant.

Therefore, what is needed is a lip implant that eliminates, or at least significantly reduces, the above-described complications. Moreover, instrumentation and a method for insertion of this new lip implant are needed. Finally, a method that is easily reversible is needed.

BRIEF DESCRIPTION OF THE DRAWINGS

FIG. 1 is a perspective view of a lip implant according to one embodiment of the present disclosure.

FIG. 2 is a cross-sectional view of the lip implant of FIG. 1 taken along the line 2-2.

FIG. 3 is a perspective view of a lip implant instrument according to one embodiment of the present disclosure.

FIG. 4 is a side view of the lip implant instrument of FIG. 3.

FIG. 5 is a cross-sectional view of the lip implant instrument of FIG. 4 taken along the line 5-5.

FIG. 6 is a schematic view of a lip for receiving the lip implant according to the present disclosure.

FIG. 7 is a perspective view of a lip implant according to another embodiment of the present disclosure.

FIG. 8 is a perspective view of a lip implant according to yet another embodiment of the present disclosure.

FIG. 9 is a perspective view of a lip implant according to yet another embodiment of the present disclosure.

FIG. 10 is a perspective view of a lip implant according to yet another embodiment of the present disclosure.

FIG. 11a is a sectional view of a lip implant according to yet another embodiment of the present disclosure.

FIG. 11b is a sectional view of a lip implant according to yet another embodiment of the present disclosure.

FIG. 11c is a sectional view of a lip implant according to yet another embodiment of the present disclosure.

DESCRIPTION

Referring to FIG. 1, a lip implant for implantation into a lip of a patient (not shown) is generally referred to by reference numeral 10. In one embodiment, the lip implant is integrally formed of medical grade silicone and is substantially solid as shown in the cross-section of FIG. 2. The implant can be manufactured by a variety of methods including, but not limited to, injection molding, cast molding, extrusion, or cutting from a larger, solid block.

The lip implant 10 is formed to have a substantially uniform level of hardness as can be measured by the durometer A-scale rating. Of course, hardness can be measured in manners other than via durometer A-scale ratings. In one embodiment, the lip implant 10 has a durometer rating of ten (10) or less resulting in a relatively soft lip implant. In such an embodiment, the lip implant 10 may include a skin 12, also formed of silicone, having a higher durometer rating to provide the lip implant with structural integrity and manageability. Accordingly, the provision of the skin 12 may aid in handling or manageability of the lip implant 10. However, the provision for a skin 12 is not always necessary, and the lip implant 10 with a durometer rating of ten (10) or less may be used without the need for an external skin. Of course, the particular durometer rating of the lip implant 10 may vary depending on the particular firmness desired. Also, the lip implant 10 may have a varying durometer rating of 0 to 50, resulting in a lip implant having a non-uniform hardness.

The lip implant 10 is shaped to have a substantially circular cross-section (FIG. 2). The diameter of the lip implant 10 is substantially uniform along the longitudinal axis of a middle portion 14 of the lip implant. The diameter of the middle portion 14 of the lip implant 10 can vary depending on the desired thickness of the lip implant. For instance, the diameter of the lip implant 10 may be between 2-10 millimeters.

The middle portion 14 of the lip implant 10 defines a pair of end portions 16. The end portions 16 are tapered in diameter such that the diameter of the lip implant 10 along the end portions decreases from the middle portion 14 to the ends of the lip implant. The middle portion 14 and the end portions 16 of the lip implant 10 cooperate to define the length of the lip implant, which can vary depending on the desired length of the lip implant. For instance, the length of the lip implant 10 may be between 5-8 centimeters.

Referring to FIGS. 3-5, a lip instrument for use in implanting the lip implant 10 is generally referred to by reference numeral 20. The lip instrument 20 includes a pair of arms 22a, 22b coupled together at a pivot point 24 in any conventional manner to provide for relative pivotal movement of the arms about a pivotal axis P (FIG. 4). Proximal to the pivotal axis P, the arms 22a, 22b include a pair of integrally formed ring-like members 26a, 26b, respectively, which define a pair of finger openings 28a, 28b. A pair of protrusions 30a, 30b extend towards one another from the ring-like members 26a, 26b, respectively, to prevent over-rotation of the arms 22a, 22b.

Distal to the pivotal axis P, the arms 22a, 22b include a pair of integrally formed curved clamping members 32a, 32b, respectively, which cooperate to grasp the lip implant 10 (FIG. 1) as will be further described with respect to the method of insertion. Referring to FIG. 5, the clamping members 32a, 32b include an outer generally convex surface 34a, 34b, respectively, and a corresponding inner generally concave surface 36a, 36b.

The inner surfaces 36a, 36b of the clamping members 32a, 32b face one another such that closing of the clamping members defines a generally circular area for grasping the lip implant 10 (FIG. 1). The inner surfaces 36a, 36b are formed of a non-crushing surface in order to prevent damage to the lip implant 10 (FIG. 1) when squeezed between the clamping members. In one embodiment, the inner surfaces 36a, 36b are formed of carbide.

Referring to FIG. 6, a lip region 40 of a patient (not shown) to receive the lip implant is depicted. The lip region 40 includes an upper lip 42 and a lower lip 44, which meet at a pair of commissures 46a, 46b. The commissures 46a, 46b are substantially equidistant from a midline M of the lip region 40. A tunnel 48, as is generally illustrated in phantom in FIG. 6, is formed through the lower lip 44 for reasons to be described with respect to the method for insertion.
Method for Insertion In operation, referring to FIG. 6, the lip region 40 is prepared for insertion of the implant by administering a local or regional anesthetic. Incisions are then made at each commissure 46a, 46b of the lip region 40 via a conventional scalpel or scissors. For sake of clarity, the method of insertion will be described with respect to insertion of the lip implant 10 into the lower lip 44 although it will be understood that the lip implant can be inserted into the upper lip 42 as well.

Initial formation of the tunnel 48 is then performed with conventional curved iris scissors (not shown). The iris scissors are inserted into the lower lip 44 via the incision at commissure 46a to dissect the tunnel 48 towards the midline M of the lip region 40. In a like manner, the iris scissors are then inserted through the incision at commissure 46b on the opposite side of the lip region 40 to dissect the tunnel 48 towards the midline M of the lip region. Such dissection culminates in the initial formation of the tunnel 48 through the lower lip 44. The tunnel 48 is then widened via manipulation of the iris scissors or lip instrument 20 to complete the formation of the tunnel.

After establishing the tunnel 48, the lip instrument 20 is inserted into the lower lip 44 via the incision at commissure 46a and the tunnel 48 such that the clamping members 32a, 32b extend through the tunnel enabling a portion of the clamping members to extend outside of the incision at commissure 46b. The lip instrument 20 is then actuated to grasp the lip implant 10 between the clamping members 32a, 32b. The lip implant 10 is then drawn into the lower lip 44 via the lip instrument 20 until it is positioned appropriately within the tunnel 48 whereupon the lip implant is released from the lip instrument.

A conventional suture, such as a chromic or nylon suture, is then used to close the incisions at commissures 46a, 46b. Antibiotic ointment may be applied to the incisions at commissures 46a, 46b as a prophylaxis against infection. Ice may be applied indirectly to the lip region 40 to reduce swelling.

Thus, as described, insertion of the lip implant 10 is accomplished simply and quickly and in an uninterrupted manner. Thus, many of the problems associated with previous lip augmentation techniques can be eliminated with the use of the lip implant 10. Furthermore, this process is completely reversible if desired.

ALTERNATES AND EQUIVALENTS

It is understood that a variety of alternative lip implants are contemplated by this disclosure. For example, and referring now to FIG. 7, a lip implant 70 substantially similar in all respects to the lip implant 10 of FIGS. 1 and 2, other than those features described below, has a middle portion 72 that includes a section 74 having a non-uniform diameter.

In another alternative embodiment, and referring now to FIG. 8, a lip implant 80 substantially similar in all respects to the lip implant 10 of FIGS. 1 and 2, other than those features described below, includes a middle portion 82 having a non-uniform diameter along the entire length of the middle portion.

In yet another alternative embodiment, and referring now to FIG. 9, a lip implant 90 substantially similar in all respects to the lip implant 10 of FIGS. 1 and 2, other than those features described below, is substantially non-uniform in diameter along the length of the implant. The lip implant 90 is reduced in diameter at a middle portion 92 thereof.

In operation, the lip implants 70, 80 and 90 of FIGS. 7, 8 and 9, respectively, are inserted into the lower lip 44 (FIG. 6) of the patient in a substantially similar manner as described above. Thus, the embodiments of FIGS. 7, 8 and 9 enjoy the advantages of that of FIG. 1 with respect to providing a structurally sound and safe lip implant for lip augmentation purposes.

In yet another alternative embodiment, and referring now to FIG. 10, an alternative lip implant 100 substantially similar in all respects to the lip implant 10 of FIGS. 1 and 2, other than those features described below, is shaped to have a substantially elongated cross-section, which is substantially uniform in size along the length of the implant. In operation, the lip implant 100 is inserted into the lower lip 44 (FIG. 6) of the patient in a substantially similar manner as described above. After insertion into the lower lip 44, the lip implant 100 may be further sized to correspond to the shape of the lip. For example, the ends of the lip implant 100 may be cut in a tapered fashion such that the lip implant is customized to the particular shapes and contours of the lower lip 44.

As can be appreciated, the materials used in forming the lip implants of the present disclosure can be varied to include additional materials for use with silicone or alternative materials other than silicone. For example, the lip implants 10, 70, 80, 90, 100 and other embodiments of the lip implant of the present disclosure may alternatively be formed of urethane rather than silicone.

Moreover, referring to FIG. 11a, an alternative lip implant 110a includes an inner core region 112a formed of expanded polytetraflouroethylene (PTFE) such as Gore-Tex®, and an outer shell 114a formed of silicone. The silicone used for the outer shell 114a provides the lip implant 110a with additional manageability. More importantly, the presence of the outer silicone shell 114a aids in preventing tissue-adherence associated with the use of expanded PTFE.

It is understood that other types of outer shells are contemplated for the lip implant 110. For example, in some embodiments, the outer shell 114a may be in the form of a polymer coating, such as Parylene™, which can be applied to the exterior of the inner core region 112a to provide structural integrity and manageability. Accordingly, any number of materials including but not limited to silicone, urethane, expanded PTFE, and biocompatible polymers, and any combination of such materials may be used to form the lip implant 110a.

In another embodiment, and referring to FIG. 11b, an alternative lip implant 110b includes an inner core region 112b formed of materials such as liquid silicone, silicone gel or beads, cohesive silicone gel or beads, biocompatible oil, saline or a biocompatible hydrogel material. The lip implant 110b further includes an outer shell 114b, which may be formed of a variety of materials including but not limited to silicone, urethane and biocompatible polymer (such as Parylene™). As can be appreciated, the outer shell 114b encloses the inner core region 112b and may be formed in an impermeable or semipermeable manner such that there is minimal or no leakage of the inner core region 112b through the outer shell.

In still other embodiments, and referring to FIG. 11c, an alternative lip implant 110c includes an inner core region 112c, which may take the form of a hollow space defined by an outer shell 114c. In such an embodiment, the inner core region 112c can be filled with a gas such as air. Moreover, the outer shell 114c may be formed of a variety of materials including but not limited to silicone, urethane and biocompatible polymers. As can be appreciated, the outer shell 104c may be formed in an impermeable manner such that there is no leakage of gas from the inner core region 112c through the outer shell.

While the invention has been particularly shown and described with reference to embodiments thereof, it is understood by those skilled in the art that various changes in form and detail may be made therein without departing from the spirit and scope of the invention. For example, although a plurality of shapes of the lip implant 10 is described, these shapes are merely representative of the variety of shapes that the lip implant may take. Thus, the lip implant 10 is not limited to the longitudinal or cross-sectional shapes as described.

Moreover, the tapered end portions 16 of the lip implant 10 may be removed resulting in a lip implant having a rod-like shape. Still further, the degree of taper and the length of the end portions 16 may be varied to accommodate the various desires or needs of implant patients.

Still further, the clamping members 32a, 32b of the lip instrument 20 may be removable attached to the lip instrument such that various other clamping members may be used therewith. For instance, various degrees of curvature may be required of the clamping members resulting in the need to interchange the clamping members.

Furthermore, the inner surfaces 36a, 36b of the clamping members 32a, 32b may be formed of a variety of materials other than carbide.

Still further, during insertion of the lip implant 10 into the lower lip 44, the incision may be made in the general commissure region on each side of the lip region 40 and such insertion is not limited to an exact commissure point.

It is also understood that all spatial references, such as "diameter", "longitudinal," "increase," and "decrease" are for illustrative purposes only and can be varied within the scope of the invention. Accordingly, all such modifications are intended to be included within the scope of this invention as defined in the following claims.

What is claimed is:

1. A lip implant sized for insertion in a human lip, the lip implant comprising:
   a first biocompatible solid material having a first durometer rating, the first biocompatible solid material comprising:
      a first middle portion defining an outside surface and having a longitudinal center axis and a geometric center point; and
      a pair of first tapered end portions between which the first middle portion longitudinally extends, the first tapered end portions defining respective outside surfaces, the first tapered end portions being symmetric about a transverse axis that is perpendicular to the longitudinal center axis of the first middle portion and extends through the geometric center point of the first middle portion;
      wherein the first biocompatible solid material is symmetric about the longitudinal center axis of the first middle portion, and is also symmetric about the transverse axis;
   and
   an outer shell surrounding the first biocompatible solid material, the outer shell being formed of a second biocompatible solid material having a second durometer rating, the second durometer rating being higher than the first durometer rating, the second biocompatible solid material comprising:
      a second middle portion defining inside and outside surfaces, the inside surface of the second middle portion contacting the outside surface of the first middle portion; and
      a pair of second tapered end portions between which the second middle portion extends, the second tapered end portions being symmetric about the transverse axis, each of the second tapered end portions defining inside and outside surfaces, the respective inside surfaces of the second tapered end portions contacting respective ones of the outside surfaces of the first tapered end portions;
      wherein the second biocompatible solid material is symmetric about the longitudinal center axis of the first middle portion; and
      wherein the second biocompatible solid material is symmetric about the transverse axis;
   wherein the entirety of the implant is generally shaped to correspond to the shape of said lip.

2. The lip implant of claim 1 wherein the first biocompatible solid material comprises silicone.

3. The lip implant of claim 1 wherein the first biocompatible solid material comprises expanded PTFE.

4. The lip implant of claim 1 wherein the first biocompatible solid material comprises urethane.

5. The lip implant of claim 1 wherein the first biocompatible solid material comprises a biocompatible polymer.

6. The lip implant of claim 1 wherein the second biocompatible solid material comprises silicone.

7. The lip implant of claim 1 wherein the second biocompatible solid material comprises a polymer coating.

8. The lip implant of claim 1 wherein the second biocompatible solid material comprises expanded PTFE.

9. The lip implant of claim 1 wherein the second biocompatible solid material comprises urethane.

10. The lip implant of claim 1 wherein the second biocompatible solid material comprises a biocompatible polymer.

* * * * *